United States Patent [19]

Isenberg

[11] 4,158,166
[45] Jun. 12, 1979

[54] COMBUSTIBLES ANALYZER

[75] Inventor: Arnold O. Isenberg, Monroeville, Pa.

[73] Assignee: Westinghouse Electric Corp., Pittsburgh, Pa.

[21] Appl. No.: 744,898

[22] Filed: Nov. 24, 1976

[51] Int. Cl.$^2$ ............................................ G01N 27/42
[52] U.S. Cl. ..................... 324/29; 204/1 T; 204/195 S; 73/27 R
[58] Field of Search .................... 324/29, 36; 204/1 S, 204/195 R, 195 S; 73/23, 27, 30

[56] References Cited

U.S. PATENT DOCUMENTS

| | | | |
|---|---|---|---|
| 3,061,826 | 10/1962 | Willenborg | 73/27 R |
| 3,149,921 | 9/1964 | Warner | 204/1 T |
| 3,558,280 | 1/1971 | Panson et al. | 73/27 R |
| 3,607,084 | 9/1971 | Mackey | 73/27 R |
| 3,691,023 | 9/1972 | Ruka et al. | 204/195 S |

*Primary Examiner*—M. Tokar
*Attorney, Agent, or Firm*—M. P. Lynch

[57] ABSTRACT

An oxygen ion conductive solid electrolyte electrochemical cell is employed to pump oxygen for combustible reaction with fuel constituents of a combustibles gas environment which diffuse through an aperture of a housing. The housing in combination with the solid electrolyte electrochemical cell forms an internal chamber. The EMF established across the electrodes of the solid electrolyte electrochemical cell pumps sufficient oxygen for complete combustion with the fuel diffusing through the aperture into the internal chamber. The resulting current of the solid electrolyte electrochemical is indicative of the rate of diffusion of the fuel or combustibles constituent through the aperture. The rate of diffusion is proportional to the fuel or combustibles content of the combustibles gas environment.

An EMF measuring circuit connected to an auxiliary pair of electrodes associated with the solid electrolyte electrochemical cell are used to sense the condition wherein the atmosphere within the internal chamber changes between a reducing atmosphere and an oxidizing atmosphere. This EMF indication can be used to identify a predetermined level of pumping electrical potential at which variations in the solid electrolyte electrochemical cell current is indicative of the rate of diffusion of the fuel or combustibles constituent through the aperture.

6 Claims, 6 Drawing Figures

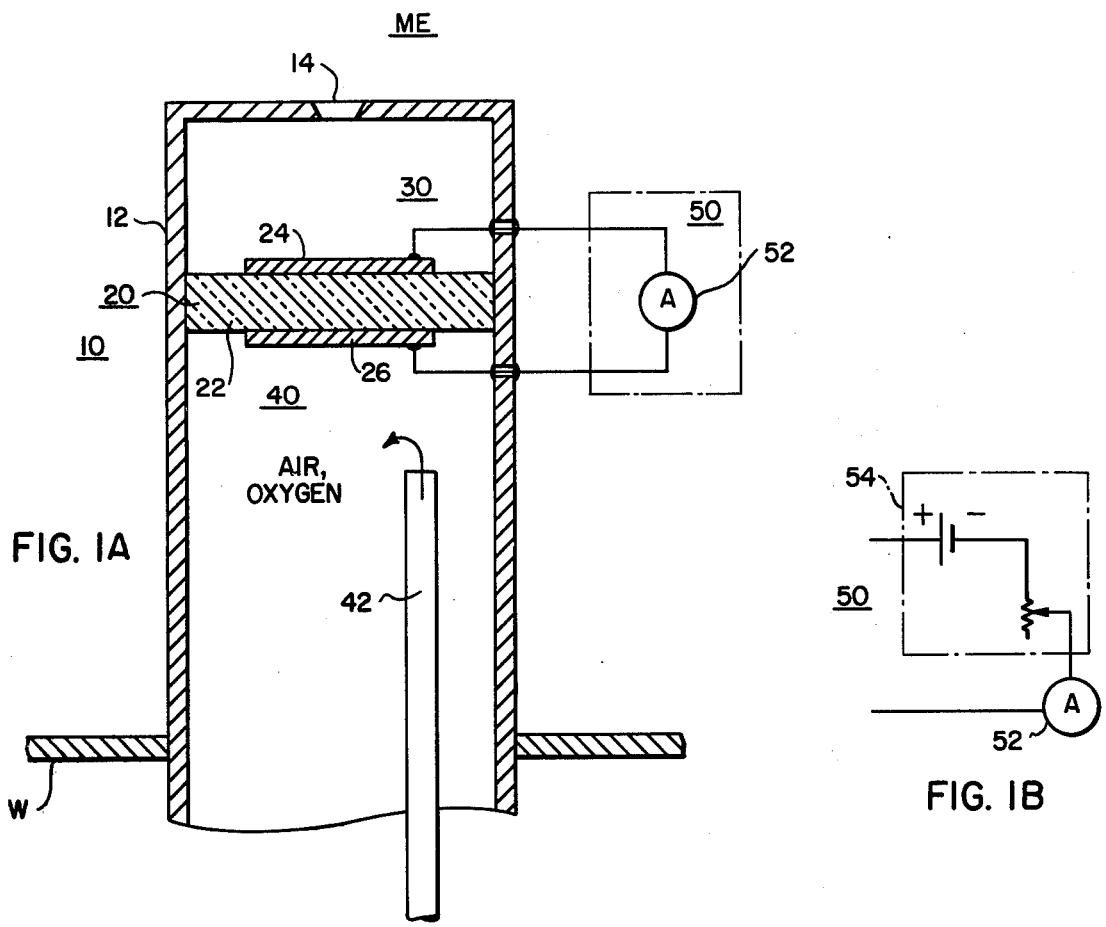
FIG. 1A
FIG. 1B
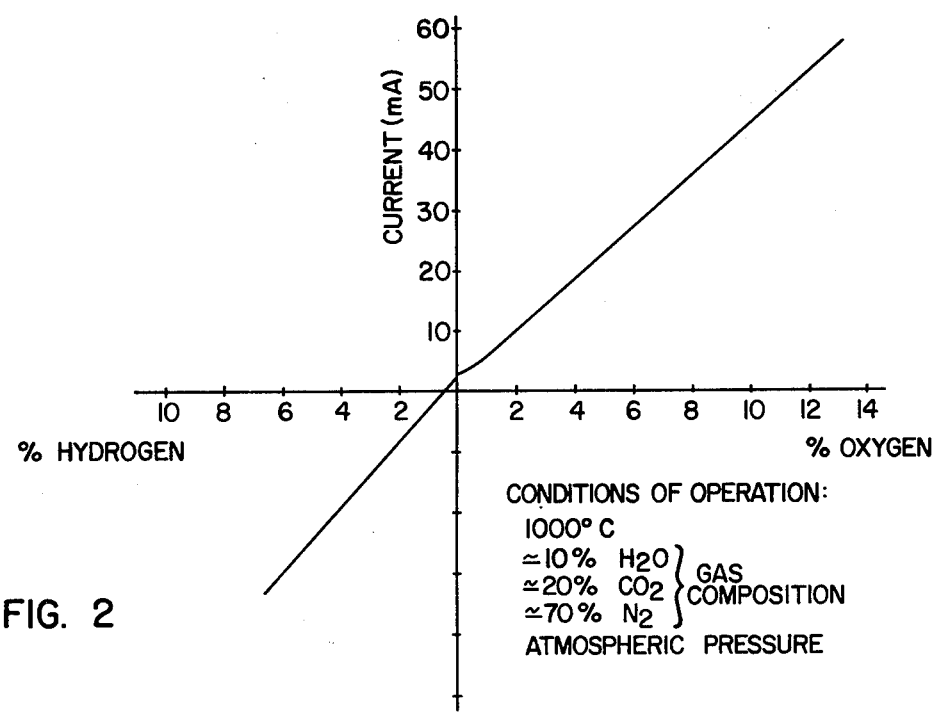
FIG. 2
CONDITIONS OF OPERATION:
1000° C
≃10% $H_2O$
≃20% $CO_2$  } GAS COMPOSITION
≃70% $N_2$
ATMOSPHERIC PRESSURE

COMBUSTIBLES ANALYZER

CROSS-REFERENCE TO RELATED APPLICATION

This application is related to the inventor's pending application, Ser. No. 637,998, entitled "Improved Gas Analysis Apparatus", filed Dec. 5, 1975 and assigned to the assignee of the present invention.

BACKGROUND OF THE INVENTION

The application of a physical adapter including a gas diffusion limiting aperture in combination with a solid electrolyte electrochemical cell is described in the above-identified cross-referenced related application which is incorporated herein by reference.

While the gas analyzer concept disclosed in the above-identified application provides an improved gas sensor apparatus for use in measuring gas constituents such as oxygen, sodium, etc., the concept as disclosed does not teach the gas diffusion aperture adapter in combination with the solid electrolyte electrochemical cell for monitoring combustibles or fuel constituents, of a combustibles gas environment. The term combustibles gas environment as used herein defines a gas environment wherein the combustibles or fuel constituents are in excess of the free oxygen.

In the non-combustibles sensing application described in the above-identified related application, the solid electrolyte electrochemical cell functions to pump the gas constituent of interest, i.e., oxygen, from an internal chamber formed by the combination of the solid electrolyte electrochemical cell and the gas aperture adapter. The diffusion rate of oxygen is proportional to the resulting current of the solid electrolyte electrochemical cell. Inasmuch as the rate of diffusion of the gas constituent of interest through the aperture is proportional to the content of the gas constituent in the gas environment, the solid electrolyte electrochemical cell current is a measurement of the presence of the non-combustible gas constituent of interest in the gas environment. In the invention of the above-identified application as well as that of the present application, the gas diffusion limiting aperture is the prime element in measuring a gas constituent and the solid electrolyte electrochemical cell functions in a secondary manner, i.e., not as a gas measuring element but rather as a gas pumping element.

In contrast to the above-identified related application wherein solid electrolyte electrochemical cell functions to pump the gas constituent of interest from the internal chamber formed by the gas aperture adapter and the solid electrolyte electrochemical cell, in the present invention a gas different from the gas constituent of interest is introduced into the internal chamber to combust with combustibles constituent diffusing through the aperture. This produces a differential pressure of the combustibles constituent across the aperture and establishes a diffusion of the combustible constituent from the combustible gas environment through the aperture into the internal chamber. The pumping potential is established at a level such that sufficient oxygen is introduced into the internal chamber to react with and deplete the combustibles constituent present in the internal chamber. The solid electrolyte electrochemical cell current resulting from the pumping of oxygen into the internal chamber is a function of the diffusion rate of the combustibles constituent through the aperture. This in turn is proportional to the combustibles content of the combustibles gas environment being monitored. The current of the solid electrolyte electrochemical cell is monitored as a measurement of the combustibles content of the combustibles gas environment.

An EMF measuring circuit indicates changes in the atmosphere of the internal chamber between a reducing atmosphere and an oxidizing atmosphere. This indication provides a basis for establishing the pumping potential at a level sufficient to assure introduction of sufficient oxygen to deplete the combustibles present in the internal chamber.

BRIEF DESCRIPTION OF THE DRAWINGS

The invention will become more readily apparent from the following exemplary description in connection with the accompanying drawings:

FIG. 1A is a schematic illustration of an embodiment of the invention;

FIG. 1B is an alternate electrical circuit for use with the embodiment of FIG. 1A;

FIG. 2 is a graphical illustration of the operation of the embodiment of FIG. 1A;

DESCRIPTION OF THE PREFERRED EMBODIMENT

Figure 5:
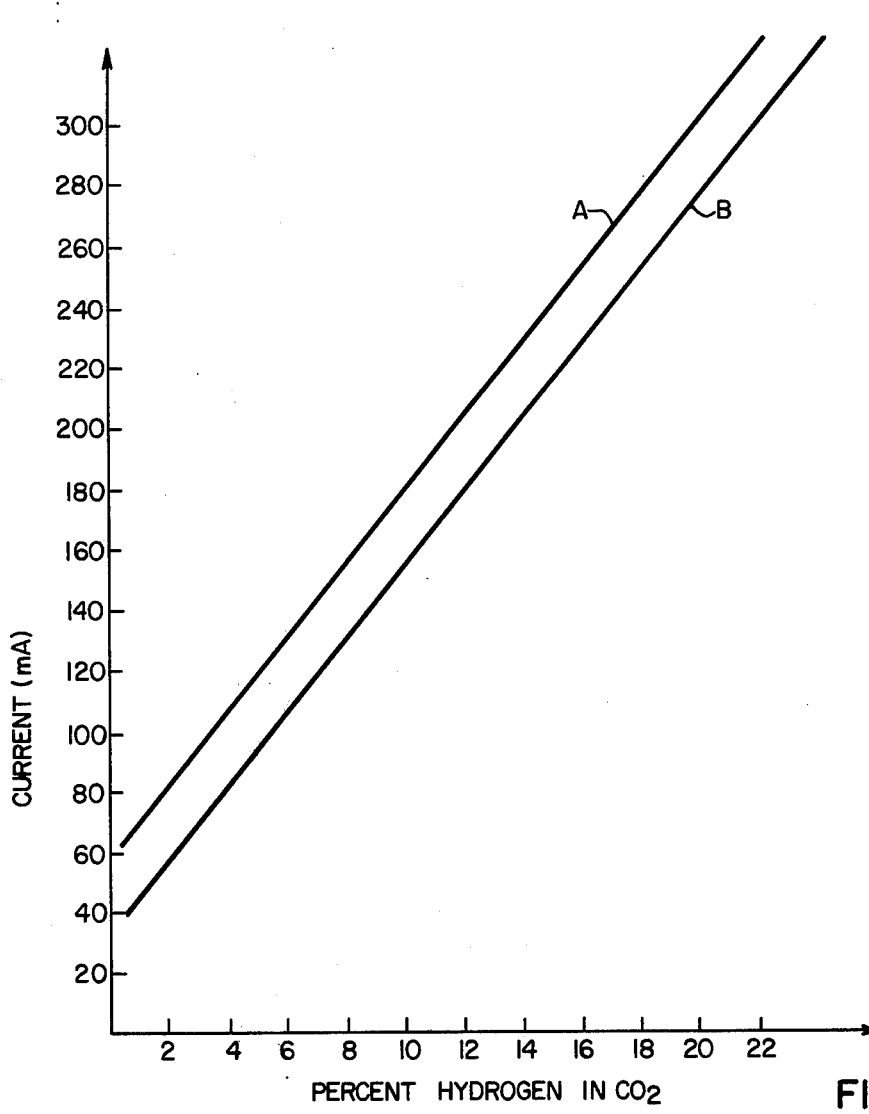
FIGS. 4 and 5 are graphical illustrations of the operation of the embodiment of FIG. 3.

While the solid electrolyte electrochemical cell employed herein functions as a pump rather than a gas measuring device and thus could be replaced by an equivalent device for pumping an oxygen containing gas, the solid electrolyte electrochemical cell is a particularly convenient device for implementing the invention.

Referring to FIG. 1A there is schematically illustrated a combustibles sensor probe 10 comprising a closed end tubular housing member 12 having a gas diffusion limiting aperture 14 in the closed end and a solid electrolyte electrochemical cell 20 sealed within said tubular housing 12 to define an internal chamber 30 and an air or oxygen chamber 40. The solid electrolyte electrochemical cell 20 consists of an oxygen ion conductive solid electrolyte member 22, and electrodes 24 and 26 disposed on opposite surfaces thereof. The composition and operation of the solid electrolyte electrochemical cell 20 is well known in the art, and is described in detail in U.S. Pat. No. 3,400,054, issued Sept. 3, 1968, assigned to the assignee of the present invention, and incorporated herein by reference.

The combustibles sensor probe 10 is schematically illustrated as being inserted through the wall W of a containment and exposed to a combustibles gas environment ME, previously defined as being a gas environment wherein the combustibles content exceeds that of the free oxygen. The temperature of the environment ME is assumed to be between 300° C. and 1000° C., the operating temperature range of conventional solid electrolyte electrochemical cells.

In the absence of adequate ambient temperature conditions, separate heating of the cell 20 can be employed. A typical implementation for internally heating the probe 10 is described in U.S. Pat. No. 3,546,086, issued Dec. 8, 1970 and assigned to the assignee of the present invention.

In the most basic embodiment of the invention, the electrical circuit 50 connected to the electrodes 24 and 26 consists solely of an ammeter 52. The mechanism relied upon for pumping oxygen introduced into the oxygen reference chamber 40 from a remote oxygen or air supply source (not shown) via oxygen inlet tube 42 is the EMF across electrodes 24 and 26 resulting from the differential oxygen partial pressure existing between the internal chamber 30 and the oxygen chamber 40. The EMF established in accordance with the well-known Nernst equation establishes a transfer of oxygen ions through the oxygen ion conductive solid electrolyte 22 from the electrode 26 to the electrode 24 wherein the oxygen reacts to deplete the combustibles constituent in the internal chamber 30. This reaction will continue until the combustibles present in the internal chamber 30 are depleted and a combustibles differential pressure is established across the aperture 14 to maintain a diffusion of the combustibles constituent from the monitoring volume ME through the aperture 14 into the internal chamber 30. The size of the aperture 14 is selected such that the resulting current is proportional solely to the diffusion rate of the combustibles constituent through the aperture. Aperture sizes are described in detail in the above referenced related application. The current of the solid electrolyte electrochemical cell 20, under the conditions where the EMF across the solid electrolyte electrochemical cell 20 is sufficient to deplete the combustible constituent of the internal chamber 30, is an indication of the rate of diffusion of the combustibles constituent through the aperture 14. The diffusion rate in turn is proportional to the combustibles content of the monitored environment. Thus, the current, as measured by the ammeter 52, is a measurement of the combustibles content of the monitored environment ME. Typical combustibles include hydrogen, methane, carbon monoxide, etc.

The selection of a gas source of oxygen is a design choice. It is apparent that a solid oxygen source, i.e., a metal-metal oxide composition, could be maintained in contact with electrode 26.

While the electrical circuit 50 of FIG. 1A supports the operation and discussion of the combination of the apertured tubular housing 12 and the solid electrolyte electrochemical cell 20, another implementation of the electrical circuit 50 is illustrated in FIG. 1B wherein a variable potential DC power supply 54 is combined with the ammeter 52. The variable potential DC power supply 54 establishes a predetermined voltage across the electrodes 24 and 26 of a polarity to pump oxygen to achieve the condition wherein the combustibles present in the internal chamber 30 are depleted and the cell current as measured by the ammeter 52 is a measurement of the diffusion rate of the monitored combustibles constituent, i.e., hydrogen, defined by the aperture 14.

It is apparent that the embodiment of FIG. 1A can be used to measure both oxygen in an oxygen gas environment, in accordance with the teachings of the referenced application, as well as combustibles in a combustibles gas environment as described herein. A graphical illustration of the probe embodiment of FIG. 1A operating in both an oxygen and combustibles sensing mode is depicted in FIG. 2.

Figure 3:
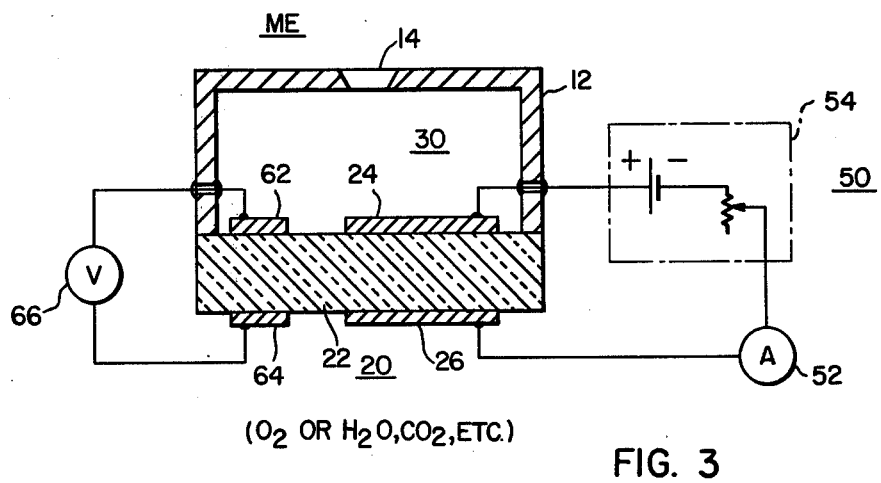
FIG. 3 is a sectioned schematic illustration of an alternate embodiment of the invention.

A modification to the combustibles sensor probe 10 of FIGS. 1A and 1B is illustrated in FIG. 3. EMF sensing electrodes 62 and 64 are disposed on opposite surfaces of the solid electrolyte 22. A change between a reducing and oxidizing atmosphere in the internal chamber 30 will cause cell 20 to produce significant change in the EMF signal developed at electrodes 62 and 64. Voltmeter 66 responds to the EMF signal and provides an indication as to when the atmosphere in the internal chamber 30 changes between reducing and oxidizing.

Figure 4:
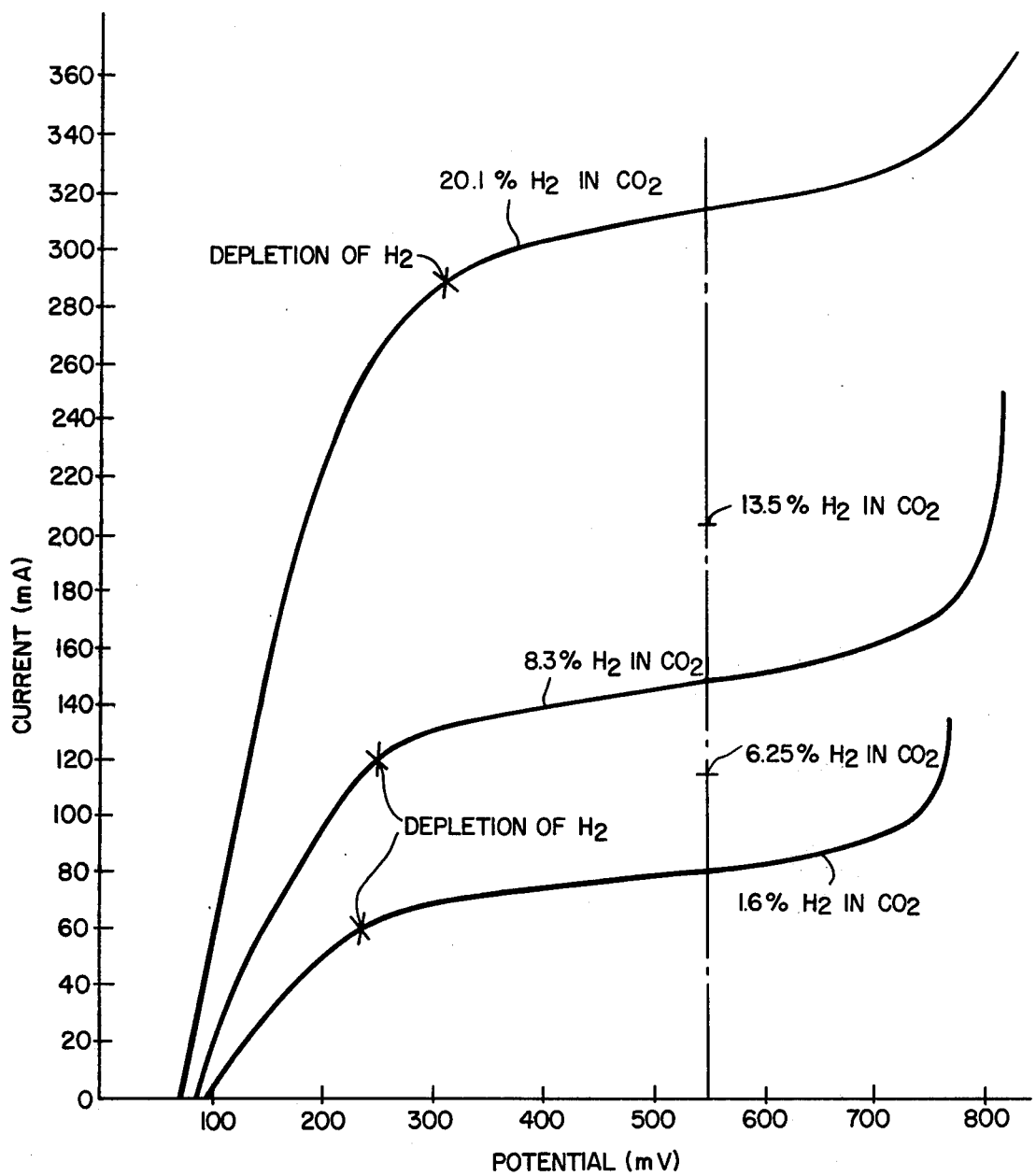

The operation of the combustible sensor embodiment of FIG. 3 is graphically illustrated in FIGS. 4 and 5. Graphical plots A, B and C of FIG. 4 illustrate the operation of combustible sensor probe 10 for three different percentages of hydrogen in carbon dioxide gas mixtures. The left-hand portion of the graph corresponds to the initial conditions wherein insufficient oxygen is present in the internal chamber 30 to deplete the combustible content thus establishing a reducing atmosphere at the electrode 24. As the oxygen pumping potential, established either by the oxygen partial pressure differential of FIG. 1A or the variable DC power supply 54 of the electrical circuit 50 of FIG. 1B, increases, a threshold condition X as monitored by voltmeter 66, is achieved wherein the oxygen introduced into the internal chamber 30 is adequate to deplete the combustibles present thus converting the reducing atmosphere at the electrode 24 to an oxidizing atmosphere. Thus a pumping potential is selected to be of a magnitude to the right of the threshold condition X, such as that corresponding to 550 millivolts for the condition of the graphical illustration of FIG. 4. Having established the rather arbitrary pumping potential, variations in the current of the solid electrolyte electrochemical cell 20 at this pumping potential, as measured by the ammeter 52, provide a measurement of the content of the combustibles constituent, i.e. hydrogen, in the monitored environment ME. The current measurement corresponding to the 550 millivolts pumping potential of the curves of FIG. 4 are plotted as a percent of hydrogen in carbon dioxide as curve A of FIG. 5. Curve B of FIG. 5, which is parallel to curve A, represents the current measurements corresponding to threshold X of the curves of FIG. 4.

While the embodiments of FIGS. 1A, 1B and 3 correspond to a probe configuration wherein an external oxygen supply source is used, the inventive concept can also be embodied in a configuration, wherein the oxygen contained in a compound, i.e., $H_2O$, $CO_2$, present in the monitored environment ME can provide, via electrolysis of $H_2O$, $CO_2$, etc., the oxygen to be transferred into the internal chamber 30. The EMF established across the electrodes 24' and 26' of the oxygen ion conductive solid electrolyte electrochemical cell 20 pumps oxygen resulting from the electrolysis of oxygen containing compounds, i.e., $H_2O$ and $CO_2$ in the monitored gas environment through the solid electrolyte 22 for reaction with the combustibles constituent in the internal chamber 30 as described above. This approach provides a very simple and portable combustibles sensor inasmuch as there is no requirement for a separate source of oxygen.

I claim:
1. A combustibles sensor apparatus operative in a monitored combustibles gas environment to measure the combustibles constituent content, comprising,
an adapter having a means defining gas diffusion limiting aperture,
means for establishing a diffusion of a combustibles constituent of interest from a monitored combustibles gas environment through said aperture, and
means for measuring the rate of diffusion of said combustibles constituent through said aperture as an indication of the combustibles constituent content of said monitored combustibles gas environment.

2. A combustibles sensor apparatus as claimed in claim 1 wherein said means for establishing diffusion of said combustibles constituent includes means for providing a source of oxygen to combustibly react with said combustibles constituent diffusing through said aperture to establish a differential pressure of said combustibles constituent across said aperture to thereby maintain said diffusion of said combustibles constituent from said monitored combustibles gas environment through said aperture.

3. A combustibles sensor apparatus operative in a monitored combustibles gas environment to measure the combustibles constituent content, comprising, an adapter having a means defining gas limiting aperture, means for establishing diffusion of a combustibles constituent of interest from a monitored combustibles gas environment through said aperture, wherein said means for establishing diffusion of said combustibles constituent through said aperture includes a solid electrolyte electrochemical cell having an oxygen ion conductive solid electrolyte and first and second electrodes disposed on opposite surfaces thereof, said solid electrolyte electrochemical cell combined with said adapter to form an internal chamber having communication with said monitored combustibles gas environment through said aperture, said first electrode being exposed to said internal chamber, a source of oxygen being provided at said second electrode to establish an oxygen differential pressure across said solid electrolyte electrochemical cell resulting in the transfer of oxygen from said second electrode through said solid electrolyte to said first electrode to combustibly react with said combustibles constituent diffusing through said aperture and thereby establish a differential partial pressure of said combustibles constituent across said aperture to maintain diffusion of said combustibles constituent from said monitored combustibles environment through said aperture, said solid electrolyte electrochemical cell producing a current in response to said transfer of oxygen, the size of said aperture being such that the current is proportional solely to the diffusion rate of the combustibles constituent through the aperture, and means for measuring the current of said solid electrolyte electrochemical cell as an indication of the combustibles constituent content of said monitored combustibles gas environment.

4. The combustibles sensor apparatus as claimed in claim 3 further including EMF measuring means operatively connected to said solid electrolyte electrochemical cell to indicate changes in the atmosphere of said internal chamber between a reducing atmosphere and an oxidizing atmosphere.

5. A combustibles sensor apparatus as claimed in claim 4 wherein said monitored combustibles gas environment includes oxygen containing molecules, said second electrode being exposed to said monitored combustibles gas environment, said oxygen containing molecules functioning as said source of oxygen.

6. A combustibles sensor apparatus operative in a monitored combustibles gas environment to measure the combustibles constituent content, comprising, an adapter means having a means defining gas diffusion limiting aperture, means for establishing diffusion of a combustibles constituent of interest from a monitored combustibles gas environment through said aperture, wherein said means for establishing diffusion of said combustibles constituent through said aperture includes a solid electrolyte electrochemical cell having an oxygen ion conductive solid electrolyte and first and second electrodes disposed on opposite surfaces thereof, said solid electrolyte electrochemical cell combined with said adapter to form an internal chamber having communication with said monitored combustibles gas environment through said aperture, said first electrode being exposed to said internal chamber, a source of oxygen being provided at said second electrode, means for supplying DC voltage source connected across said electrodes of a magnitude and polarity to cause said solid electrolyte electrochemical cell to transfer oxygen from said second electrode through said solid electrolyte to said first electrode to combustibly react with said combustibles constituent diffusing through said aperture and thereby establish a differential partial pressure of said combustibles constituent across said aperture to maintain diffusion of said combustibles constituent from said monitored combustibles gas environment through said aperture, said solid electrolyte electrochemical cell producing a current in response to said transfer of oxygen, the size of said aperture being such that the current is proportional solely to the diffusion rate of the combustibles constituent through the aperture, and means for measuring the current of said solid electrolyte electrochemical cell as an indication of the combustibles constituent content of said monitored combustibles gas environment.

* * * * *